United States Patent [19]

Babin et al.

[11] 4,411,157

[45] Oct. 25, 1983

[54] CONTAMINATION-FREE TRANSFER AND PURGE APPARATUS

[76] Inventors: Eugene R. Babin, 10 Buttonball Ter., Norwalk, Conn. 06851; William R. Drago, 22 Gerry St., Greenwich, Conn. 06830

[21] Appl. No.: 382,809

[22] Filed: May 27, 1982

[51] Int. Cl.³ .............................................. G01N 1/28
[52] U.S. Cl. .................................... 73/864.81; 73/19; 436/177; 436/181
[58] Field of Search ................. 73/19, 864.81, 864.87; 422/88, 101, 103, 81; 436/177, 180, 181

[56] References Cited

U.S. PATENT DOCUMENTS 3,150,516  9/1964  Linnenbom et al. .................. 73/19
4,252,769  2/1981  Hood et al. ........................ 422/81

Primary Examiner—S. Clement Swisher
Attorney, Agent, or Firm—Alfred E. Miller

[57] ABSTRACT

A method and apparatus for introducing a sample of liquid to be analyzed for dissolved gas into an analyzer. The sample is transferred from a syringe to a bubble chamber through a valved conduit. Subsequently the volitile gas is swept out of the liquid and into an analyzer by a purge gas.

7 Claims, 3 Drawing Figures

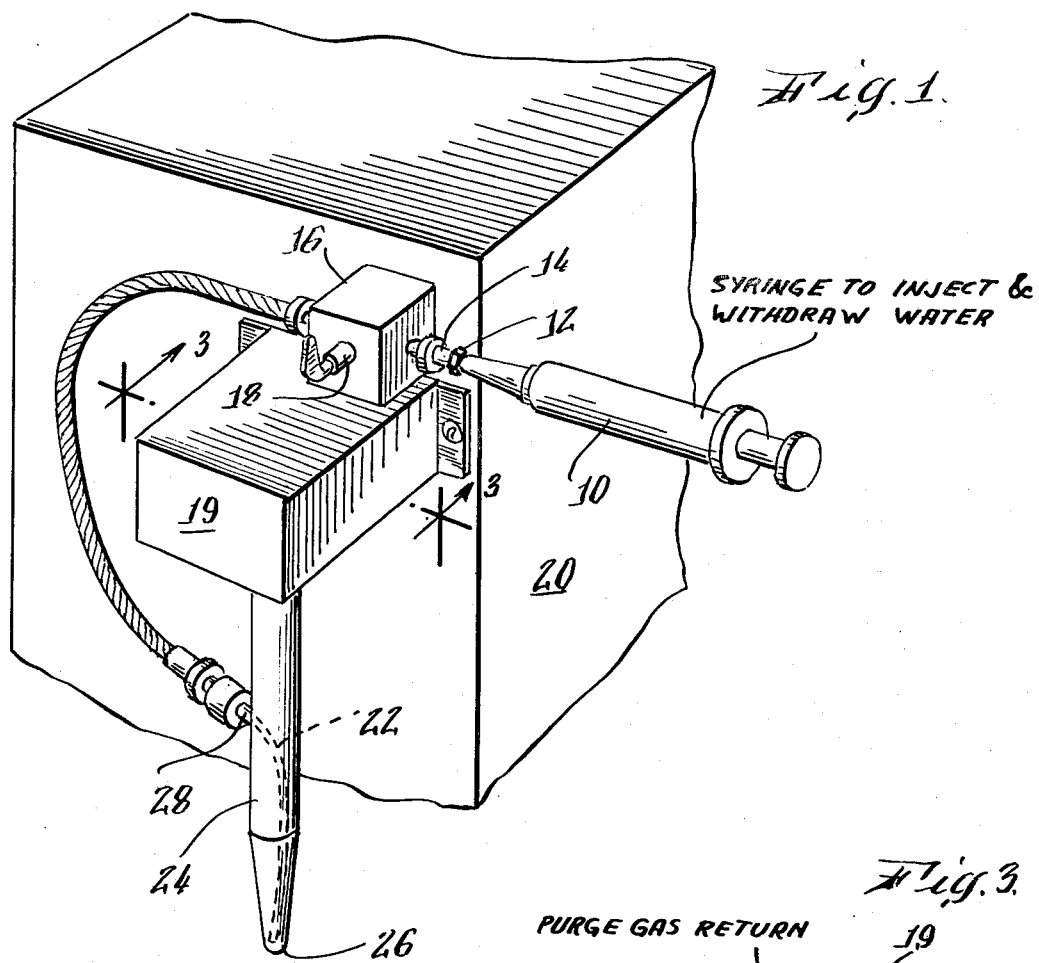
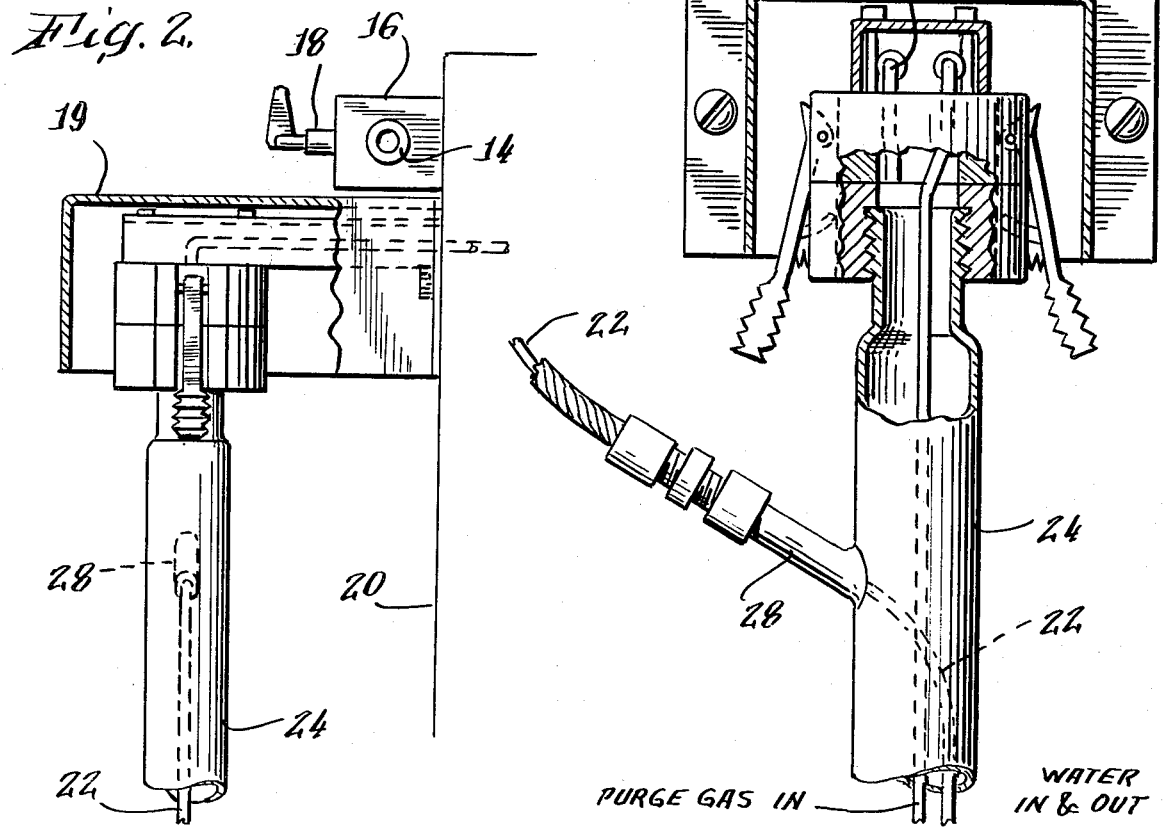

CONTAMINATION-FREE TRANSFER AND PURGE APPARATUS

The present invention relates to a device for use with a purge and trap sampler which concentrates trace amounts of volatile organic compounds on an adsorbent by purging a sample matrix with an inert gas. The purge and trap sampler is used in conjunction with either a gas chromatograph and/or a mass spectrometer. A typical application of the purge and trap sampler is the analysis of volatile organic compounds in water which are quantitatively transferred from a 5 ml. water sample on to a trap, where they are thermally back flushed on to a gas chromatography column.

A serious problem with transferring water samples to the above-described sampler in that in introducing the 5 ml. sample into the purge vessel, the sample makes contact with the atmosphere which results in introducing contamination into the sample, or even permitting some of the volatile compounds from the sample to escape to the atmosphere. This problem is particularly troublesome when continuously taking samples of drinking water for testing. Thus, in order to get a true indication of the composition of the drinking water, it is necessary to maintain the sample contamination-free.

It is an object of the present invention to provide a method and apparatus for withdrawing samples of drinking water, and introducing the same into a purge trap sampler, without contamination.

In order that the invention will be more clearly understood, it will now be disclosed in greater detail with reference to the accompanying drawings, in which:

FIG. 1 is a perspective view of the apparatus for introducing fluid samples into a purge and trap sampler device which is used in conjunction with an analytical apparatus.

FIG. 2 is a partial sectional and partial elevational view of the contamination-free transfer and purge apparatus constructed according to the teachings of the present invention, and FIG. 3 is an enlarged sectional view of a detail of construction of the purge and trap sampler to which the present apparatus is applied.

As seen in FIG. 1, a syringe 10 of a known type is filled with a water sample of a selected amount, for example 5 ml. This sample is obtained by withdrawing drinking water from 40 ml vials having a screw cap and a Teflon-coated silicon septa (not shown). After the 5 ml. sample of drinking water is withdrawn into the syringe 10, the needle is removed so that the connector cap 12 can be attached to a female connector 14 on the valve body 16. The valve body is located on the purge cap assembly unit 19. The valve 18 is in an open position thereby permitting the sample to be injected into the purge and trap sampler 20. After the sample is injected in the sampler 20, the valve 18 is closed. Thus, the sample is withdrawn from the receiving vial and introduced into the sampler apparatus 20 without any contact with the atmosphere. Consequently, the water sample is now ready to be purged, since it has been introduced through tubing 22 into the cylindrical-shaped vessel 24, having a pointed bottom portion 26 and a tubular side arm 28. It should be noted that tubing 22 extends into the vessel 24, and the end portion thereof terminates adjacent to the bottom of the pointed portion 26.

In order to withdraw the water sample, a hypodermic syringe 10 again has its connector 12 attached to the female connector 14 on the valve body 16. Thereafter, the valve 18 is opened and the plunger 10a is pulled outwardly resulting in the total withdrawal of the sample from the purge vessel 24 due to the free end of the tubing 22 extending to the bottom of the vessel.

It should be noted, that although the present method utilizes a 15 ml. modified centrifuge tube or vessel 24, a larger centrifuge tube can be utilized if a larger sample of the water or other fluid to kapparatus be analyzed is needed. It should also be noted that although the present method shows a two-way valve 18 for sample introduction and withdrawal, a three, or more, way valve may be used if it is desired to introduce other reagents in order to study the reaction products in the liquid. The purge and trap sampler device may be of the type identified as Model 7675A that is manufactured by the Hewlett-Packard Co., and forms no part of the present invention. However, it should be understood that other types of sampler units may be used effectively with the above-described apparatus. Although the present invention is described in connection with the analysis of drinking water, it should be noted that samples of other types of fluids, such as other liquids and gases can be handled by the present device in a contamination-free manner.

It should be evident that the present apparatus, constructed in accordance with the teachings of the invention, will have more integrity in the analysis of volatile organics from drinking waters and other fluids than previous known devices. The apparatus interfaces with known sampler units, and can be easily attached or removed therefrom.

While the present invention has been disclosed and described with reference to a single embodiment, it will be apparent that variations and modifications may be made therein which fall within the true spirit and scope of the invention as defined in the following claims.

What is claimed is:

1. A device for transferring a fluid sample from a container to a purge and trap sampler without exposing said fluid sample to the atmosphere including a hypodermic syringe having the fluid to be tested, comprising: a valve body provided with at least a two-way valve, means connecting said syringe to said valve body without exposing said fluid sample to the atmosphere, a purge vessel provided with a tubular side arm, a tubing connected at one end to said valve body and the free end thereof passing through said side arm with its extremity being positioned in the bottom of said purge vessel so that a contamination-free fluid sample is introduced into said sampler for processing.

2. A device as claimed in claim 1 wherein said hypodermic syringe can be reconnected to said valve body when it is desired to totally withdraw the sample from said purge vessel.

3. The device as claimed in claim 1 wherein said tubing is flexible, while said side arm is rigid.

4. A method for transferring a fluid sample from a container to a purge and trap sampler without exposing said fluid sample to the atmosphere comprising the steps of withdrawing the fluid sample from the container by means of a hypodermic syringe, connecting the syringe to a valve body on said sampler without exposing said fluid sample to the atmosphere moving a two-way valve to its open position, providing a purge vessel having a tubular-shaped side arm on said sampler, providing a tubing connected at one end to said valve body and passing the free end thereof through said side arm whereby the extremity of said tubing is positioned in the bottom of said purge vessel so that a contamination-free fluid sample is introduced into said sampler for processing.

5. The method as claimed in claim 4 and further comprising the step of disconnecting said hypodermic syringe from said valve body after said fluid sample is introduced into said sampler, and reconnecting said hypodermic syringe to said valve body after said fluid sample has been analyzed to substantially totally withdraw said fluid sample from said purge vessel.

6. The method as claimed in claim 4 wherein said fluid sample is water.

7. The method as claimed in claim 4 wherein said fluid sample is a gas.

* * * * *